United States Patent [19]
Albert et al.

[11] Patent Number: 4,739,053
[45] Date of Patent: Apr. 19, 1988

[54] 2H-V-TRIAZOLO[4-5-D]PYRIMIDINES

[75] Inventors: Bernhard Albert, Ludwigshafen; Gerhard Hoffmann, Otterstadt; Peter Neumann, Wiesloch, all of Fed. Rep. of Germany

[73] Assignee: BASF Aktiengesellschaft, Ludwigshafen, Fed. Rep. of Germany

[21] Appl. No.: 837,880

[22] Filed: Mar. 6, 1986

Related U.S. Application Data

[63] Continuation of Ser. No. 577,771, Feb. 7, 1984, abandoned.

[30] Foreign Application Priority Data

Feb. 9, 1983 [DE] Fed. Rep. of Germany ....... 3304330

[51] Int. Cl.$^4$ ............................................ C07D 487/04
[52] U.S. Cl. ....................................... 544/254; 430/59; 534/753; 534/776; 534/794; 544/118
[58] Field of Search ................................ 544/118, 254

[56] References Cited

U.S. PATENT DOCUMENTS

| | | | |
|---|---|---|---|
| 2,543,333 | 2/1951 | Parker et al. | 544/254 |
| 2,995,525 | 8/1961 | Crounse | 544/254 X |
| 3,257,204 | 6/1966 | Süs et al. | 96/1.5 |
| 3,615,385 | 5/1967 | Lind | 96/1 |
| 3,671,258 | 6/1972 | Taber | 430/600 |
| 4,157,443 | 6/1979 | Fletcher | 544/254 |
| 4,302,586 | 11/1981 | Fletcher | 544/254 |
| 4,429,029 | 1/1984 | Hoffmann et al. | 430/57 |
| 4,456,672 | 6/1984 | Eilingsfeld et al. | 430/59 |
| 4,517,270 | 5/1985 | Graser et al. | 430/58 |
| 4,533,612 | 8/1985 | Eilingsfeld et al. | 430/59 |

FOREIGN PATENT DOCUMENTS

| | | |
|---|---|---|
| 0093330 | 11/1983 | European Pat. Off. . |
| 1058836 | 11/1959 | Fed. Rep. of Germany . |
| 1117391 | 5/1962 | Fed. Rep. of Germany . |
| 1120875 | 7/1962 | Fed. Rep. of Germany . |
| 2220408 | 11/1973 | Fed. Rep. of Germany . |
| 2726116 | 12/1978 | Fed. Rep. of Germany . |
| 3304330 | 8/1984 | Fed. Rep. of Germany ...... 544/254 |
| 1556083 | 11/1979 | United Kingdom . |
| 2040940 | 9/1980 | United Kingdom . |

OTHER PUBLICATIONS

Timmis et al., Chemical Abstracts, vol. 51, 10531i--10533h, (1957).

Primary Examiner—Donald G. Daus
Assistant Examiner—D. G. Rivers
Attorney, Agent, or Firm—Keil & Weinkauf

[57] ABSTRACT

Novel 2H-v-triazolo[4,5-d]pyrimidines of the general formula

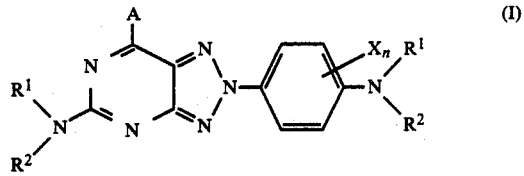

where $R^1$ and $R^2$ independently of one another are each alkyl, unsubstituted or substituted phenyl or phenalkyl, or

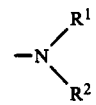

is a saturated 5-membered or 6-membered heterocyclic ring, X is alkyl, halogen or phenyl n is 0, 1 or 2, and A is

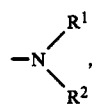

hydrogen, halogen, cyano, thiocyano, alkoxy, alkoxyalkoxy, unsubstituted or substituted phenoxy, phenylalkoxy, alkylthio, phenylthio, —S—(CH$_2$)$_m$—COO-alkyl, where m is from 1 to 4, alkylcarbonyl, benzoyl, carboxyl, carboalkoxy, alkylsulfonyl, phenylsulfonyl, an N-imidazole, benzimidazole, 1,2,3-triazole, benzotriazole, 2-mercaptobenzothiazole, 2-mercaptobenzimidazole, 2-mercaptothiazole or 2-mercapto-1,3,4-thiadiazole radical, or a radical of the formula

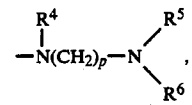

where $R^4$ is H or C$_1$–C$_4$-alkyl, p is from 2 to 5 and $R^5$ and $R^6$ are each C$_1$–C$_4$-alkyl, or

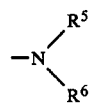

is a saturated 5-membered or 6-membered heterocyclic radical which can furthermore contain N, O and/or S as ring members, are useful charge carrier-transporting compounds in electrophotographic recording materials.

10 Claims, No Drawings

2H-V-TRIAZOLO[4-5-D]PYRIMIDINES

This application is a continuation of application Ser. No. 577,771, filed on Feb. 7, 1984, now abandoned.

The present invention relates to novel 2H-v-triazolo[4,5-d]pyrimidines and their use as charge carrier-transporting compounds in electrophotographic recording materials.

Electrophotographic processes, materials required for these, and various embodiments of the composition of recording materials have been disclosed. Advantageous materials for use in the reprography sector are those comprising a polymeric binder which can be adapted to the special requirements of the particular field of use, low molecular weight organic compounds which are soluble, even in relatively high concentration, in the binder and are capable of transporting charge carriers, and compounds, in particular dyes or pigments, which produce charge carriers when exposed imagewise to actinic light, and are capable of transferring these charge carriers to the charge-transporting compounds, with the aid of the electric field exerted from outside by the electrostatic surface charge. Depending on the field of use of the recording material, these charge carrier-producing compounds can be incorporated, as a separate layer, in a composite structure (cf. German Laid-Open Application DOS No. 2,220,408), or may be present in the form of a monodisperse solution of the dye molecules in a mixture of the binder and the charge carrier-transporting compounds (cf. German Pat. No. 1,058,836). The multi-layer electrophotographic recording material described in German Laid-Open Application DOS No. 2,220,408 comprises an electrically conductive base, a first layer which is about 0.005-2 μm thick, contains a dye and produces charge carriers when exposed to actinic light, and a second layer which is composed of organic materials, which are insulating in the dark, together with one or more charge-transporting compounds.

It has also been disclosed that photosemiconducting organic compounds may be used for the production of electrophotographic printing plates, in particular electrophotographic offset printing plates (cf. German Pat. Nos. 1,117,391 and 1,120,875 and German Published Applications DAS No. 1,522,497 and DAS No. 2,726,116).

The increased demands on reprographic systems necessitate a large variety of recording materials and systems in order that special problems can be solved in an optimum manner. The characteristics desired include high photosensitivity, good resolution and good toning properties. Inadequate toning, which is frequently objected to and which indicates unfavorable differentiation between the field strengths of the exposed and non-exposed areas, is often attributable to the fact that the recording material in the charged state possesses an excessively high conductivity in the dark, so that there is an inadequate surface charge density before imagewise exposure to actinic light.

It is an object of the present invention to provide further electrophotographic recording materials which are suitable, in particular, for the production of electrophotographic printing plates, such as offset printing plates, and which are highly photosensitive and possess good resolution and processability and low conductivity in the dark.

We have found that this object is achieved, and that improved electrophotographic recording materials which comprise an electrically conductive base, charge carrier-producing compounds or sensitizers and charge carrier-transporting compounds are obtained, if these materials contain, as charge carrier-transporting compounds, novel 2H-v-triazolo[4,5-d]pyrimidines of the formula (I)

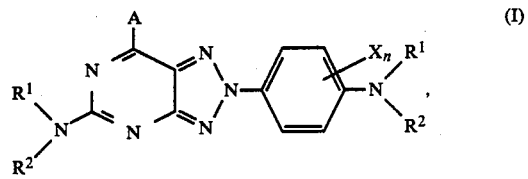

where $R^1$ and $R^2$ independently of one another are each $C_1$–$C_4$-alkyl, phenyl which is unsubstituted or substituted by chlorine, bromine, $C_1$–$C_4$-alkyl or $C_1$–$C_4$-alkoxy, or phenylalkyl of, in total, 7 to 10 carbon atoms, or

is a saturated 5-membered or 6-membered heterocyclic ring, and the two

groups can be identical or different, X is $C_1$–$C_4$-alkyl, halogen or phenyl, n is 0, 1 or 2, and A is (1)

where $R^1$, $R^2$ and

have the above meanings, (2) hydrogen, halogen, cyano or thiocyano, (3) $C_1$–$C_6$-alkoxy, $C_1$–$C_8$-alkoxy-$C_2$- or —$C_3$-alkoxy, phenoxy which is unsubstituted or substituted by Cl, Br or $C_1$–$C_4$-alkyl, phenylalkoxy of, in total, 7 to 10 carbon atoms, $C_1$–$C_{12}$-alkylthio, phenylthio which is unsubstituted or substituted by chlorine, bromine, $C_1$–$C_4$-alkyl and/or $C_1$–$C_4$-alkoxy, or —S—$(CH_2)_m$—$COOR^3$, (4) $C_1$–$C_6$-alkylcarbonyl, benzoyl which is unsubstituted or substituted by $C_1$–$C_4$-alkyl or $C_1$–$C_4$-alkoxy, carboxyl or carbo-$C_1$–$C_8$-alkoxy, (5) $C_1$–$C_4$-alkylsulfonyl or unsubstituted or $C_1$–$C_4$-alkyl-substituted phenylsulfonyl, (6)

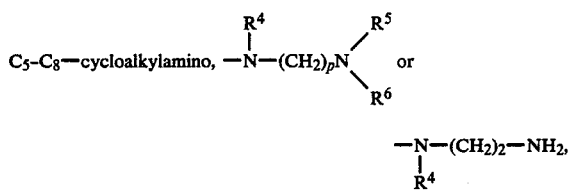

(7)

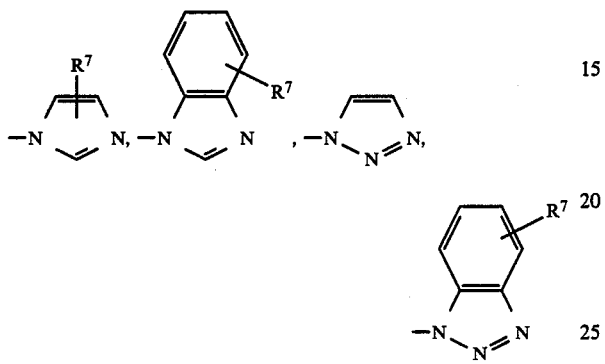

or (8)

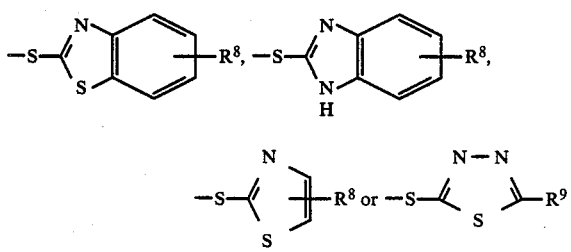

and where $R^3$ is $C_1$–$C_4$-alkyl, m is 1, 2, 3 or 4, $R^4$ is hydrogen or $C_1$–$C_4$-alkyl, $R^5$ and $R^6$ independently of one another are each $C_1$–$C_4$-alkyl, or

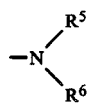

is a saturated 5-membered or 6-membered heterocyclic radical which may or may not contain N, O and/or S as further ring members, p is 2, 3, 4 or 5, $R^7$ and $R^8$ independently of one another are each hydrogen, $C_1$–$C_4$-alkyl, $C_1$–$C_4$-alkylcarbonyl, nitro, halogen or phenyl, and $R^9$ is hydrogen, $C_1$–$C_4$-alkyl, $C_1$–$C_4$-alkylcarbonyl, phenyl, thio or $C_1$–$C_4$-alkylthio.

The novel electrophotographic recording materials have a combination of very good properties, in particular high photoconductivity coupled with very low conductivity in the dark, and are hence very useful for the copying sector. They possess substantial advantages when used for the production of electrophotographic printing plates, satisfying high requirements in respect of resolution and the print run.

Specific examples of substituents $R^1$ and $R^2$ for I are $C_1$–$C_4$-alkyl, such as methyl, ethyl, n- and i-propyl, n-butyl and isobutyl, unsubstituted or substituted phenyl, such as phenyl, 2-, 3- and 4-tolyl, 2-, 3- and 4-methoxyphenyl, 2-, 3- and 4-ethoxyphenyl, 2-, 3- and 4-chlorophenyl, 2-, 3- and 4-bromophenyl, 3- and 4-ethylphenyl, 3- and 4-isopropylphenyl and 3- and 4-sec.-butylphenyl, and phenylalkyl, such as benzyl, 2- and 1-ethylphenyl, 2- and 3-propylphenyl and butylphenyl.

Examples of saturated 5-membered and 6-membered heterocyclic rings —$NR^1R^2$ are the radicals of pyrrolidinyl, piperidino, morpholino, thiomorpholino, thiomorpholino S-dioxide and N-$C_1$–$C_4$-alkyl- and N-$C_2$–$C_4$-hydroxylalkylpiperazinyl, such as N-methyl-, N-ethyl- and N-butyl-N-($\beta$-hydroxyethyl)-piperazinyl and N-($\beta$-hydroxypropyl)-piperazinyl.

Preferred radicals $R^1$ and $R^2$ are methyl, ethyl, phenyl and benzyl, and preferred radicals

are morpholino, piperidino, pyrrolidinyl and N'-$C_1$–$C_4$-alkylpiperazinyl.

Specific examples of substituents X are $C_1$–$C_4$-alkyl, such as methyl, ethyl, propyl or butyl, halogen, such as bromine, fluorine or, preferably chlorine, and phenyl; n is 1, 2 or, preferably, 0.

Suitable radicals A are:

(1)

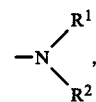

where $R^1$, $R^2$ and

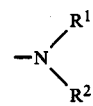

have the above meanings, and cyclohexylamino, (2) hydrogen, halogen, eg. bromine, fluorine and, preferably, chlorine, cyano and thiocyanate, (3) (a) $C_1$–$C_6$-alkoxy, eg. methoxy, ethoxy, n- and i-propoxy, n-butoxy, n-pentyloxy, hexyloxy and 2,2-dimethylpropoxy, (b) $C_1$–$C_8$-alkoxy-$C_2$- or -$C_3$-alkoxy, eg. 2-methoxyethoxy, 2-ethoxyethoxy, 2-propoxyethoxy, 2-butoxyethoxy, 2-hexyloxyethoxy, 2-octyloxyethoxy, 2-(2'-ethylhexyloxy)-ethoxy, 3-methoxypropoxy, 3-ethoxypropoxy, 3-propoxypropoxy, 3-butyloxypropoxy, 3-hexyloxypropoxy, 3-(2'-ethylhexyloxy)-propoxy and 3-octyloxypropoxy, (c) unsubstituted or substituted phenoxy, eg. phenoxy, 3- and 4-chlorophenoxy, 3- and 4-bromophenoxy, 3- and 4-methylphenoxy and 3- and 4-ethylphenoxy, (d) phenylalkoxy, eg. benzyloxy, 2-phenylethoxy and 2- and 3-phenylpropoxy, (e) $C_1$–$C_{12}$-alkylthio, eg. methyl-, ethyl-, propyl-, butyl-, hexyl-, octyl-, decyl- and dodecylmercapto, (f) unsubstituted or substituted phenylthio, eg. phenylthio, 3- and 4-chlorophenylthio, 4-methylphenylthio, 3- and 4-bromophenylthio, 3- and 4-methoxyphenylthio and 3- and 4-ethoxyphenylthio, (g) —S—(CH$_2$)$_m$—COOR$^3$, where m is 1, 2, 3 or 4 and R$^3$ is C$_1$-C$_4$-alkyl, such as methyl, ethyl, propyl or butyl.

(4) Carboxyl, and alkylcarbonyl and unsubstituted or substituted benzoyl, eg. acetyl, propionyl, butyryl, benzoyl, 4-methylbenzoyl and 4-methoxybenzoyl, and carboalkoxy, eg. carbomethoxy, carboethoxy, carbopropoxy and carbobutoxy.

(5) Alkylsulfonyl, eg. methylsulfonyl, ethylsulfonyl, phenylsulfonyl and p-tolylsulfonyl.

(6) Radicals of the formula

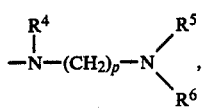

where R$^4$ is hydrogen or C$_1$-C$_4$-alkyl, and R$^5$ and R$^6$ are each C$_{1-4}$-alkyl, or

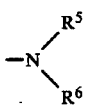

is one of the groups stated for

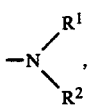

and

(7) and (8) radicals of the formulae

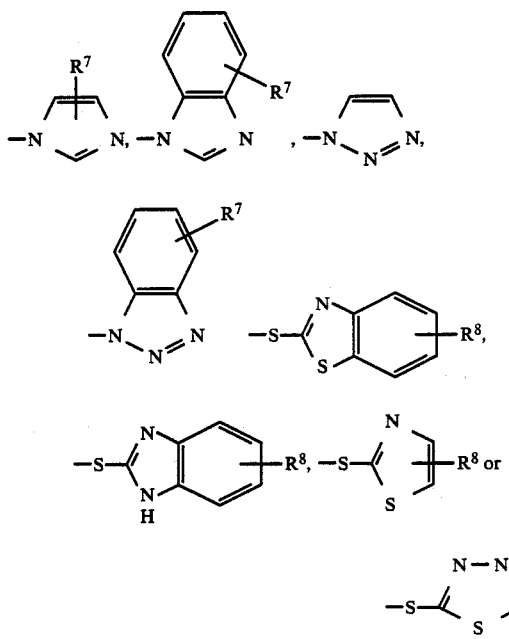

where R$^7$, R$^8$ and R$^9$ have the above meanings.

For reasons related to use, preferred substituents A from amongst those mentioned under (1) to (7) are:

(1.1) for R$^1$ and R$^2$ in

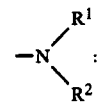

methyl and, in particular, ethyl, and for

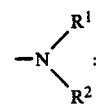

morpholino, piperidino, pyrrolidinyl and N'-C$_1$-C$_4$-alkylpiperazinyl;

(2.1) hydrogen and chlorine;

(3.1) C$_1$-C$_6$-alkoxy, in particular methoxy, ethoxy, n-propoxy, n-butoxy and 2,2-dimethylpropoxy; 2-C$_1$-C$_4$-alkoxyethoxy, in particular 2-methoxyethoxy; phenoxy; benzyloxy; C$_1$-C$_{12}$-alkylthio, in particular dodecylthio and butylthio; thiophenyl and —S—(CH$_2$)$_m$—COOR$^3$, where m is 2 and R$^3$ is C$_1$-C$_4$-alkyl, in particular methyl or ethyl;

(4.1) acetyl, propionyl, benzoyl, carbomethoxy and carboethoxy;

(5.1) benzenesulfonyl;

(6.1) —NH—(CH$_2$)$_2$NH$_2$ and

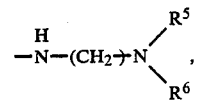

where R$^5$ and R$^6$ are each methyl or ethyl;

(7) imidazol-1-yl, benzimidazol-1-yl and benzothiazol-2-ylthio, where the phenyl radicals are unsubstituted or substituted by nitro.

Owing to their outstanding performance characteristics, particularly preferred triazolopyrimidines are those of the formula II

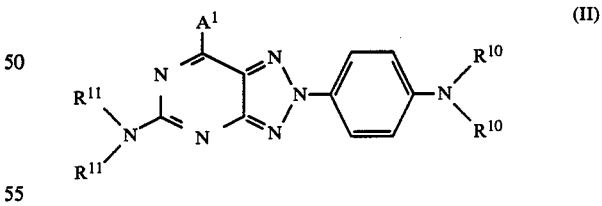

where A$^1$ is bromine, chlorine, —S—(CH$_2$)$_2$—COOC$_1$-C$_4$-alkyl, N-morpholino, N-piperidino, N-cyclohexylamino, N'-C$_1$-C$_4$-alkylpiperazino, imidazol-1-yl or C$_1$-C$_6$-alkoxy, and R$^{11}$ and R$^{12}$ can be identical or different and independently of one another are each C$_1$-C$_4$-alkyl, in particular methyl or ethyl or phenyl.

Very particularly preferred compounds (II) are those in which A$^1$ is chlorine, —S—(CH$_2$)$_2$—COOCH$_3$, N-morpholino, N-piperidino, N-cyclohexylamino, N'-methylpiperazinyl, imidazol-1-yl, methoxy, ethoxy, n-propoxy, n-butoxy or 2,2-dimethylpropoxy, and the radicals

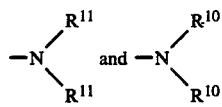

independently of one another are each dimethylamino, diethylamino or diphenylamino.

Among the compounds of the formula II, those of the formula III should be very particularly singled out:

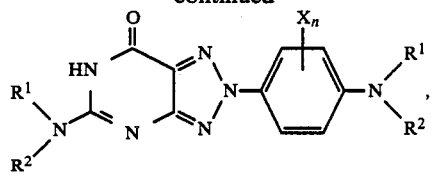

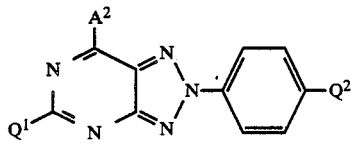

| | $A^2$ | $Q^1$ | $Q^2$ |
|---|---|---|---|
| (III a) | —Cl | —N(C$_2$H$_5$)$_2$ | —N(—⌬)$_2$ |
| (III b) | —Cl | —N(CH$_3$)$_2$ | —N(C$_2$H$_5$)$_2$ |
| (III c) | —Cl | —N(C$_2$H$_5$)$_2$ | —N(C$_2$H$_5$)$_2$ |
| (III d) | —S—C$_2$H$_4$—COCH$_3$ (O) | —N(C$_2$H$_5$)$_2$ | —N(C$_2$H$_5$)$_2$ |
| (III e) | —OCH$_3$ | —N(C$_2$H$_5$)$_2$ | —N(C$_2$H$_5$)$_2$ |
| (III f) | —OC$_2$H$_5$ | —N(C$_2$H$_5$)$_2$ | —N(C$_2$H$_5$)$_2$ |
| (III g) | —OCH$_2$—CH$_2$—CH$_3$ | —N(C$_2$H$_5$)$_2$ | —N(C$_2$H$_5$)$_2$ |
| (III h) | —O—(CH$_2$)$_3$CH$_3$ | —N(C$_2$H$_5$)$_2$ | —N(C$_2$H$_5$)$_2$ |
| (III i) | —O—CH$_2$—C(CH$_3$)$_3$ | —N(C$_2$H$_5$)$_2$ | —N(C$_2$H$_5$)$_2$ |
| (III k) | —O—CH$_2$—CH$_2$—O—CH$_3$ | —N(C$_2$H$_5$)$_2$ | —N(C$_2$H$_5$)$_2$ |
| (III l) | —N(C$_2$H$_5$)$_2$ | —N(C$_2$H$_5$)$_2$ | —N(C$_2$H$_5$)$_2$ |

Among these compounds, those of the formula (IIII) and especially those of the formulae (IIIb) and (IIIe) should be singled out.

The novel triazolo[4,5-d]pyrimidines I can be prepared by a conventional process.

For example, (I) can be prepared by the following route:

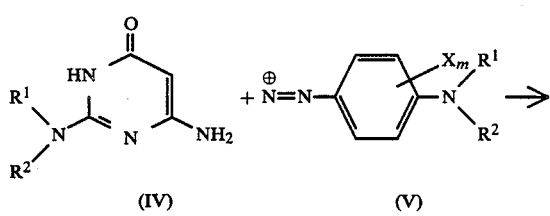

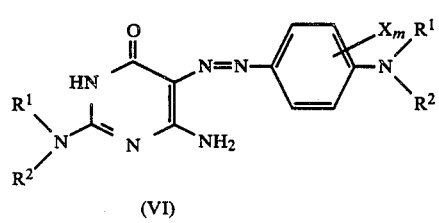

In the formulae, $R^1$, $R^2$, X and n have the above meanings. In the process, the o-aminoazo dye obtained by coupling (V) to (IV) is converted to the triazole derivative by oxidation.

The coupling of (V) to (IV) is carried out as a rule at from $-10°$ to $+20°$ C., preferably from $0°$ to $10°$ C.

A very large variety of oxidizing agents are suitable for the oxidation of (VI) to (VII), eg. chromic acid, alkali metal dichromates, hydrogen peroxide, lead tetraacetate, potassium ferricyanide, ferric chloride and copper(II) sulfate. In acidic solvents, eg. aqueous acetic acid, it is preferable to use an alkali metal dichromate, hydrogen peroxide or lead tetraacetate, while in basic solvents, eg. a pyridine/water mixture, potassium ferricyanide is preferred. The oxidative cyclization is preferably effected using copper(II) sulfate in a pyridine/water mixture. The oxidation with copper(II) salts, such as copper(II) sulfate or chloride, can also advantageously be carried out in methanol or a methanol/water mixture in the presence of an ammonium or amine salt, such as mono- or dialkanolamine. The oxidative cyclization is carried out at from 70° to 100° C., preferably from 90° to 100° C.

The oxygen in the resulting oxo compound (VII) is then replaced with chlorine by a conventional method:

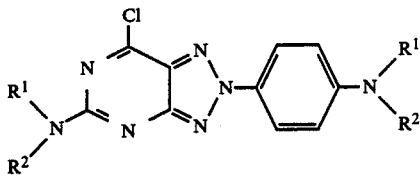

VIII

This can be done using various chlorinating agents, eg. phosphorus oxychloride, in the presence or absence of a tertiary organic base, eg. triethylamine, diethylaniline, phosphorus pentachloride or thionyl chloride, for example in the presence of dimethylformamide.

The chlorine compound (VIII) can then be converted to a compound of the formula (I), where A is not chlorine, by a conventional method, by reaction with a compound of the formula AM (IX), where M is hydrogen or one equivalent of a metal and A has the above meanings, in a suitable solvent, in the presence or absence of an acid acceptor.

Examples of suitable solvents for this reaction are methylene chloride, chlorobenzene, tetrahydrofuran, dimethylformamide, N-methylpyrrolidone and mixtures of these.

Preferred acid acceptors for the process are tertiary amines, eg. triethylamine, tripropylamine and tributylamine.

The Examples illustrate the preparation of triazolopyrimidines of the formula (I).

The novel triazolopyrimidines of the formulae (I), (II) and (III) are very useful as charge carrier-transporting compounds in electrophotographic layers, and can advantageously be employed both in single-layer and in multi-layer recording systems on an electrically conductive base.

The compounds of the formula (II), and in particular those of the formula (III) have proven useful for this purpose. Among the latter, the compounds of the formulae (IIIa) to (IIIc) and (IIIe) should be very particularly singled out.

Suitable single-layer systems comprise, preferably on a conductive base, a layer of (a) from 45 to 75 parts by weight of a binder, (b) from 30 to 60, in particular from 35 to 50, parts by weight of one of the charge carrier-transporting compounds used according to the invention, (c) if appropriate from 5 to 25 parts by weight of another, essentially inactive binder and (d) from 0.05 to 0.8 part by weight of a compound which produces charge carriers when exposed to actinic light, in particular a suitable dye. The layer is advantageously applied from an about 5% strength by weight solution in a suitable organic solvent onto the clean conductive base so as to give a layer which is about 0.8–40 μm thick after the solvent has been evaporated off in the air. The thickness of the layer depends on the intended use, and is, in particular, from 0.8 to 6 μm in the case of electrophotographic printing plates.

Suitable multi-layer systems possess, on an electrically conductive base, for example (a) a charge carrier-producing layer and (b) a charge-transporting layer comprising from 30 to 60 parts by weight of one or more charge carrier-transporting compounds of the formula (I) and from 45 to 75 parts by weight of an organic binder, with or without from 5 to 25 parts by weight of further additives which improve the mechanical properties of the layer. The first layer is advantageously applied onto the base in a thickness of from 0.005 to 5, in particular from 0.1 to 0.9, μm, as a solution in a suitable solvent. After this layer has been applied, the second layer is applied so that a layer from 5 to 25, in particular from 7 to 15, um thick results after the composite structure has been dried.

In principle, any electrically conductive base can be employed, provided that it is suitable for the field of use of the recording material. Depending on the field of use, preferred bases are aluminum, zinc, magnesium, copper or polymetallic sheets, for example crude or pretreated, eg. roughened and/or anodized, aluminum sheets, aluminum foils, polymer films with metallized surfaces, such as polyethylene terephthalate films coated with aluminum by vapor deposition, and special electrically conductive papers. Bases for printing plates are advantageously from 0.08 to about 0.3 mm thick.

The use for which the recording material is intended determines which type of organic binder is suitable for the layers. Examples of suitable binders for the copying sector are cellulose ethers, polyester resins, polyvinyl chlorides, polycarbonates, copolymers, eg. styrene/-maleic anhydride or vinyl chloride/maleic anhydride copolymers, or mixtures of these. The choice of binders is governed in particular by their film-forming and electrical properties, their adhesion on the base and their solubility properties. Particularly suitable binders in recording materials for the production of electrophotographic printing plates, especially offset printing plates, are those which are soluble in basic aqueous or alcoholic solvents. These are, in particular, substances possessing groups which make them soluble in alkali, eg. anhydride, carboxyl, sulfonic acid, phenol or sulfonimide groups. Preferred binders are those which in particular have a high acid number, and are readily soluble in basic aqueous-alcoholic solvent systems and have a mean weight average molecular weight of from 800 to 80,000, in particular from 1,500 to 50,000. Examples of suitable binders are copolymers of methacrylic acid and methacrylates, in particular those of styrene with maleic anhydride and of styrene, methacrylic acid and methacrylates, provided that they possess the above solubility properties. Although it is known that binders possessing free carboxyl groups cause an undesirable increase in the conductivity of electrophotographic layers in the dark and hence lead to poor toning results, such binders can be readily made compatible with the benzotriazoles used in accordance with the invention. Thus, we have found that styrene/maleic anhydride/acrylic or methacrylic acidcopolymers which contain from 5 to 50% by weight of maleic anhydride as copolymerized units and from 5 to 35, in particular from 10 to 30, % by weight of acrylic or methacrylic acid as copolymerized units give satisfactory electrophotographic layers having adequate conductivity in the dark. They are highly soluble in washout solutions containing 75% by weight of water, 23% by weight of isobutanol and 2% by weight of sodium carbonate, but are insoluble in fountain solutions conventionally used for offset plates.

Examples of suitable charge carrier-producing compounds or sensitizers for single-layer systems, as also used for the production of electrophotographic printing plates, are triarylmethane dyes, xanthene dyes and cyanine dyes. Very good results were obtained with the compounds according to the invention, of the formula I, and rhodamine B (C.I. 45170), rhodamine 6 G (C.I. 45160), malachite green (C.I. Basic Green 4, C.I. 42000), methyl violet (C.I. 42535) or crystal violet (C.I. 42555). In multilayer systems, the dye or the pigment is present in a separate charge carrier-producing layer. In this case, azo dyes, phthalocyanines, isoindoline dyes and perylenetetracarboxylic acid derivatives are particularly effective. Good results are achieved with perylene-3,4:9,10-tetracarboxylic acid diimide derivatives, as described in German Laid-Open Applications DOS No. 3,110,954 and DOS No. 3,110,960.

Depending on the use to which it is put, the electrophotographic recording material according to the invention can contain conventional additives, for example leveling agents and plasticizers in the photoconductive layer, or adhesion promoters between the base and the layer.

The novel electrophotographic recording materials have a combination of very good properties, in particular high photoconductivity coupled with very low conductivity in the dark, and are hence very useful for the copying sector.

These materials possess substantial advantages when used for the production of electrophotographic printing plates, satisfying high requirements in respect of resolution and print run. When the plate is processed in a reprographic camera, the high photosensitivity permits the exposure time to be reduced by up to about a half compared with conventional materials. The very crisp image reproduction results in good resolution, and, as a result of high charge contrast, it is also possible to obtain good reproduction of fine dots in the light tonal range. Furthermore, exposure of the layers results in very low residual potentials, and the images obtained during toning are free from ground in the non-image areas. The spectral sensitivity decreases sharply at 600 nm, so that the layers can be handled in red light, without image loss occurring.

Electrophotographic offset printing plates are produced in a conventional manner by charging the electrophotographic recording material electrostatically by means of a high-voltage corona, following this directly by imagewise exposure, developing the resulting latent electrostatic charge image by means of a dry or liquid toner, fixing the toner in a downstream melting process and removing the non-toned photosemiconducting layer by means of a suitable washout solvent. The resulting printing plate can then be prepared in a conventional manner for offset printing, this preparation comprising, for example, hydrophilizing and gumming the water-bearing surface.

The Use Examples which follow illustrate the use, according to the invention, of triazolopyrimidines of the formula (I). Parts and percentages are by weight.

I. Preparation of the triazolopyrimidines

EXAMPLE 1

1.1: A solution of 69 parts of sodium nitrite in 160 parts of water is added to a stirred solution of 200.5 parts of N,N-diethyl-p-phenylenediamine hydrochloride in 250 parts of concentrated hydrochloric acid and 500 parts of water at from 0° to 5° C. in the course of 30 minutes. After 30 minutes, a little urea is added, and the resulting solution of the diazonium salt is added dropwise, at from 5° to 10° C., to a stirred suspension of 182 parts of 2-diethylamino-4-aminopyrimid-6-one in 1,450 parts of concentrated hydrochloric acid and 1,250 parts of water. 30 minutes after completion of the addition, 50% strength sodium hydroxide solution is added dropwise until the pH reaches 6, the mixture is stirred overnight, the precipitate is filtered off under suction, and the residue is washed with water and dried under reduced pressure.

Yield: 286 parts of a compound of the formula (VI), where $R^1$ and $R^2$ are each $-C_2H_5$ and m is 0.

Melting point: 239° C.

1.2: A solution of 75 parts of $CuSO_4.5H_2O$ in 320 parts of water is added dropwise, at 70° C., to 36 parts of the azo compound obtained as described in 1.1, in 160 parts of pyridine. The temperature is then slowly increased to the reflux temperature, the mixture is kept at this temperature for 5 hours, and air is passed through the solution during this period.

When the mixture has cooled, the precipitate is filtered off under suction, washed with water and dried under reduced pressure.

Yield: 25 parts of a compound (VII) in which $R^1$ and $R^2$ are each $-C_2H_5$ and m is 0.

Melting point: 242° C. (recrystallized from toluene).

| | Analysis: $C_{18}H_{25}N_7O$ (M. 355) | | | |
|---|---|---|---|---|
| | C | H' | N | O |
| calculated | 60.83 | 7.09 | 27.58 | 4.50% |
| found | 60.5 | 7.1 | 28.5 | 4.7%. |

1.3: 78.3 parts of phosphorus oxychloride are added dropwise, at 10° C., to a suspension of 30.2 parts of the pyrimidone obtained as described in 1.2, in 250 parts of chlorobenzene. When the addition is complete, the mixture is slowly heated to 50° C., and is kept at this temperature for 6 hours. The excess oxychloride is then distilled off under reduced pressure from a waterpump, the amount distilled off being replaced by the same amount of chlorobenzene, so that the volume of liquid in the flask is not reduced. When the oxychloride has been removed, the mixture is diluted with 200 parts of methylene chloride, the solution is washed with ice-cold water and dried over magnesium sulfate, and the solvents are finally removed under reduced pressure to give a dark yellow oil which slowly crystallizes on standing.

Yield: 25 parts of a compound (II) in which $A^1$ is Cl and $R^{10}$ and $R^{11}$ are each $-C_2H_5$ (IIIc).

Melting point: 124°–126° C.

EXAMPLE 2

6.3 parts of N-methylpiperazine in 27 parts of methylene chloride are added dropwise, at room temperature, to a solution of 10.6 parts of the chlorine compound obtained as described in 1.3, in 135 parts of methylene chloride and 3.6 parts of triethylamine. The mixture is stirred for 5 hours at 40° C. and then cooled, after which it is extracted by shaking twice with water and then dried, and the solvent is distilled off. The resulting dark yellow oil crystallizes slowly.

Yield: 9.3 parts of a compound of the formula (II), where $A^1$ is

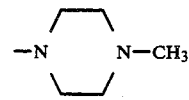

and $R^{10}$ and $R^{11}$ are each $C_2H_5$.

Melting point: 94°–95° C.

| Analysis: $C_{23}H_{35}N_9$ (M 437) | | | |
|---|---|---|---|
| | C | H | N |
| calculated | 63.13 | 8.06 | 28.81% |
| found | 63.2 | 8.2 | 28.1%. |

EXAMPLE 3

10.2 parts of a 30% strength methanolic sodium methylate solution are added dropwise to 10.6 parts of the chlorine compound obtained as described in 1.3, in 120 parts of methanol. The reaction mixture is stirred for 5 hours at 50° C. and then evaporated down under reduced pressure, 270 parts of methylene chloride are added, the mixture is extracted by shaking several times with water and dried over $MgSO_4$, and the solvent is then removed under reduced pressure.

Yield: 11.5 parts of a methoxy compound of the formula (II), where $A^1$ is $OCH_3$ and $R^{10}$ and $R^{11}$ are each $-C_2H_5$. (IIIe).

Melting point: 103°–105° C.

| Analysis: $C_{19}H_{27}N_7O$ (M 369) | | | | |
|---|---|---|---|---|
| | C | H | N | O |
| calculated | 61.77 | 7.37 | 26.54 | 4.33% |
| found | 61.9 | 7.5 | 26.2 | 4.2% |

EXAMPLE 4

3.5 parts of triethylamine are added to a solution of 8.9 parts of the chlorine compound obtained as described in 1.3, in 200 parts of methylene chloride, and a solution of 7.8 parts of methyl β-mercaptopropionate in 30 parts of methylene chloride is added dropwise in the course of 15 minutes. Stirring is carried out overnight at room temperature, after which the reaction mixture is extracted by shaking twice with water, and the organic phase is dried, and then evaporated down under reduced pressure. The resulting oil is purified by chromatography with a 4:1 toluene/ethyl acetate mixture over silica gel.

Yield: 3.5 parts of a compound of the formula (II), where $A^1$ is

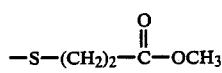

and $R^{10}$ and $R^{11}$ are each $-C_2H_5$. (IIId).

Melting point: 72°–74° C.

EXAMPLE 5

3.5 parts of triethylamine and 9.3 parts of 5(6)-nitrobenzimidazole are added to a solution of 10.6 parts of the chlorine compound obtained as described in Example 1.3, in 200 parts of methylene chloride and 50 parts of dimethylformamide. The mixture is refluxed for 8 hours, cooled and then extracted by shaking with water, and the organic phase is dried with $MgSO_4$ and evaporated down.

The crude product is recrystallized from isobutanol.

Yield: 5.4 parts of a compound of the formula (II), where $A^1$ is

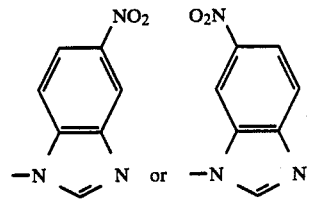

and $R^{10}$ and $R^{11}$ are each $-C_2H_5$.

Melting point: 218°–220° C.

EXAMPLE 6

6.1: The procedure described in Example 1.1 is followed, except that 51 parts of 4-aminotriphenylamine are used in the diazotization, and 30 parts of 2-dimethylamino-4-aminopyrimid-5-one are used as the coupling component.

The azo compound of the formula

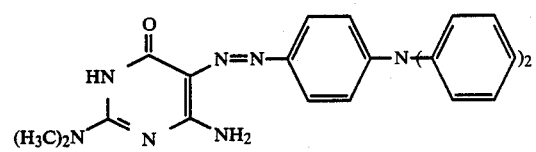

is obtained.

6.2: Using a procedure similar to that described in Example 1.2, the azo compound prepared according to 6.1 is converted to the corresponding oxotriazolopyrimidine of the formula

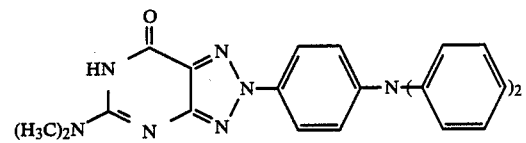

Melting point: 282°–285° C.

6.3: Using a procedure similar to that described in Example 1.3, the oxo compound from 6.2 is converted to 2-(4'-diphenylamino-phenyl)-5-dimethylamino-7-chlorotriazolo[4,5-d]pyrimidine.

Melting point: 165°–167° C.

EXAMPLE 7

7.1: The procedure described in Example 1.1 is followed, except that 43 parts of 4-aminotriphenylamine are used as the diazo component. The azo compound of the formula

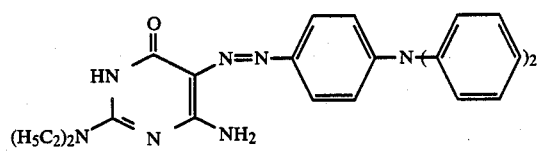

is obtained.

7.2: Using a procedure similar to that described in 1.2, the azo compound obtained according to 7.1 is converted to the oxotriazolopyrimidine of the formula

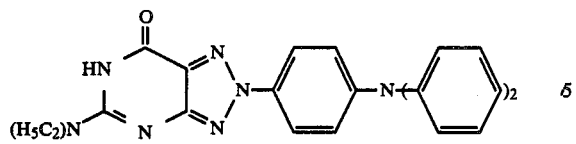

Melting point: 262°–264° C.

7.3: Using the procedure described in Example 1.3, the oxotriazolopyrimidine obtained according to 7.2 is converted to the chlorine compound of the formula

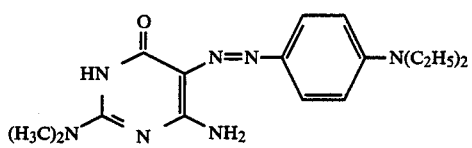

(IIIa)

Melting point: 139°–141° C.

EXAMPLE 8

8.1: The procedure described in Example 1.1 is followed, except that 154 parts of 2-dimethylamino-4-oxo-6-aminopyrimidine are used as the coupling component.

Yield: 270 parts of the azo compound of the formula

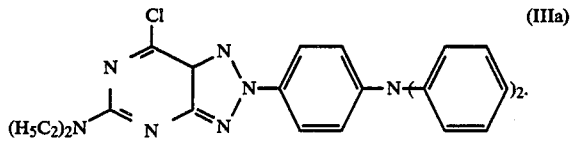

8.2: Using the process described in Example 1.2, the azo compound prepared according to 8.1 is converted to the triazolopyrimidine of the formula

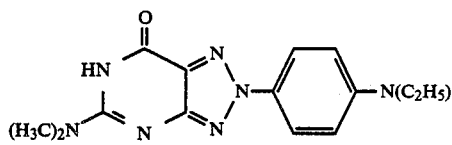

8.3: Using the procedure described in Example 1.3, the oxotriazolopyrimidine obtained according to 8.2 is converted to the 7-chloro compound.

Melting point: 165°–167° C.

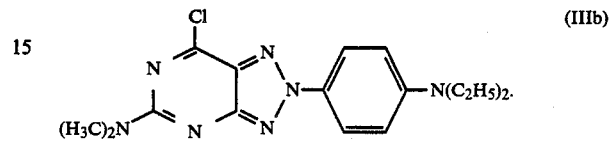

(IIIb)

EXAMPLES 9 TO 46

Using procedures similar to those described in Examples 2 to 5, the 7-chlorotriazolopyrimidine prepared according to Examples 1, 6, 7 or 8 is converted to a compound of the formula

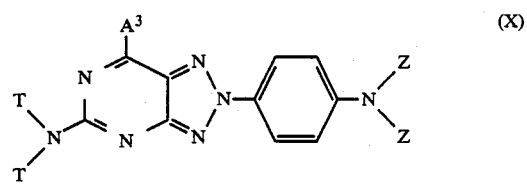

(X)

where $A^3$, Z and T have the meanings given in the Table below.

| Example No. | T | Z | $A^3$ | Melting Point (°C.) |
|---|---|---|---|---|
| 9 | —C$_2$H$_5$ | —C$_2$H$_5$ | —S—(CH$_2$)$_{11}$—CH$_3$ | 49–51 |
| 10 | —C$_2$H$_5$ | —C$_2$H$_5$ | —N⏜O (morpholino) | 158–159 |
| 11 | —C$_2$H$_5$ | —C$_2$H$_5$ | —N⏜ (pyrrolidino) | 170–171 |
| 12 | —C$_2$H$_5$ | —C$_2$H$_5$ | —N(C$_2$H$_5$)$_2$ | 105–107 |
| 13 | —C$_2$H$_5$ | —C$_2$H$_5$ | —N(—CH$_2$—CH—C$_2$H$_5$)$_2$<br>           \|<br>           C$_4$H$_9$(n) | oil |
| 14 | —C$_2$H$_5$ | —C$_2$H$_5$ | —N—CH$_2$—CH=CH$_2$<br>  H | 136–138 |
| 15 | —C$_2$H$_5$ | —C$_2$H$_5$ | —S—(CH$_2$)$_2$COOCH$_3$ | 72–74 |
| 16 | —C$_2$H$_5$ | —C$_2$H$_5$ | —N(imidazolyl) | 163–164 |

-continued

| Example No. | T | Z | A³ | Melting Point (°C.) |
|---|---|---|---|---|
| 17 | —CH₃ | —C₂H₅ | —N(morpholino) | 191–192 |
| 18 | —CH₃ | —C₂H₅ | —N(pyrrolidino) | 169–170 |
| 19 | —CH₃ | —C₂H₅ | —N(imidazolyl) | 163–164 |
| 20 | —CH₃ | —C₂H₅ | —N(C₂H₅)₂ | oil |
| 21 | —C₂H₅ | —C₂H₅ | —SCN | 248–250 |
| 22 | —C₂H₅ | —C₂H₅ | —I | 252 |
| 23 | —C₂H₅ | —C₂H₅ | —H | 120–123 |
| 24 | —C₂H₅ | —C₂H₅ | —N(piperidino) | 132–133 |
| 25 | —C₂H₅ | —C₂H₅ | —S—(CH₂)₃—CH₃ | oil |
| 26 | —C₂H₅ | —C₂H₅ | —OC₂H₅ | 107–109 |
| 27 | —C₂H₅ | —C₂H₅ | —N(CH₃)₂ | 135–137 |
| 28 | —C₂H₅ | —C₂H₅ | —N(n-C₄H₉)₂ |  |
| 29 |  |  | —N(piperazinyl)N—CH₂—CH₂—OH | 154–160 |
| 30 |  |  | —N(H)—(CH₂)₂—N(CH₃)₂ | 110–114 |
| 31 |  |  | —N(H)—(CH₂)₂—NH₂ | 89–90 |
| 32 |  |  | —CN | 103–106 |
| 33 |  |  | —SO₂—C₆H₅ | 237–240 |
| 34 |  |  | —N(piperazinyl)N—CH₃ | 93–95 |
| 35 |  |  | —N(benzimidazolyl) | 103–106 |
| 36 |  |  | —O—CH₂—CH₂—CH₃ | 107–109 |
| 37 |  |  | —O—(CH₂)₃—CH₃ | 109–111 |
| 38 |  |  | —O—CH₂—CH₂—O—CH₃ | 95–97 |
| 40 |  |  | —O—CH₂—C(CH₃)₃ | 149–151 |

-continued

| Example No. | T | Z | A³ | Melting Point (°C.) |
|---|---|---|---|---|
| 41 | | |  | 90–93 |
| 42 | | | 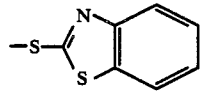 | 133–136 |
| 43 | | | 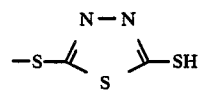 | 89–92 |
| 44 | | | 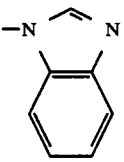 5(6)-NO₂ | 218–220 |
| 45 | | | 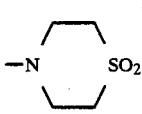 | 234–236 |

II Use of the triazolopyrimidines (I)

1. The measured xerographic values A to G given in the Use Examples are determined as follows:

The layers are charged uniformly to a surface potential of 600 volt by means of a corona at a direct current voltage of −7.5 kV at a distance of 1 cm, and are then exposed to white light from a xenon lamp with an illumination power of about 0.85 mW.cm⁻². The following measurements were carried out:

A: Time, in milliseconds (ms), during which the surface potential present before exposure falls to half its value (300 V) on exposure to actinic light.

B: Decrease in potential, in volt (V), which occurs in the same time in the dark as the result of the conductivity of the layers.

C: Surface potential, in volt (V), reached after a charging time of 20 seconds.

D: Decrease in potential in %, based on measured value C, which occurs in the dark in the course of 20 seconds.

E: Decrease in potential as a result of exposure to actinic light, in %, based on the starting potential directly before exposure.

F: Change in potential per second at the beginning of exposure (V/s).

G: Potential difference in volt (V) between exposed and non-exposed areas of the charged layer.

USE EXAMPLES 1 TO 5

A layer comprising 60 parts of a chlorinated perylene-3,4:9,10-tetracarboxylic acid diimide bis-benzimidazole with a chlorine ciontent of about 38% and 50 parts of a copolymer of vinyl chloride, acrylic acid and a maleic acid diester is applied, as a charge carrier-producing layer, in a thickness of about 0.55 μm, onto a polyethylene terephthalate film provided, by vapor deposition, with a conductive aluminum layer of about 300 Å thickness.

A charge-transporting layer comprising 55 parts of a commercial binder based on a polycarbonate and having a melting range of from 220° to 230° C. and 40 parts of one of the triazolopyrimidines shown in Table 1 is applied, from solution in ethyl acetate, onto the above charge carrier-producing layer, the solvent is evaporated off in the air and drying is carried out for 30 minutes at 80° C., the resulting layer being 12 μm thick.

The recording materials obtained were tested as described under II.1). The measured values A, B and C determined are summarized in Table 1.

TABLE 1

Measured xerographic values for the recording materials

| Use Example | Triazolopyrimidine from Example | Measured values | | |
|---|---|---|---|---|
| | | A [ms] | B [V] | C [V] |
| 1 | 7.3 | 190 | 0.25 | 2,100 |
| 2 | 8.3 | 195 | 0.2 | 1,600 |
| 3 | 1.3 | 150 | 0.3 | 2,000 |
| 4 | 4 | 155 | 0.85 | 1,050 |
| 5 | 3 | 170 | 0.2 | 1,300 |

As shown by the measurements, the electrophotographic recording materials containing the triazolopyrimidines according to the present invention possess high photoconductivity and low conductivity in the dark. Thus, for example, the layer of Use Example 1 exhibits a decrease in potential from 600 to 599.8 volt in the course of about 0.2 second in the dark, while the same layer, when exposed at an illuminating power of 0.85 mW.cm⁻² for the same time, exhibits a decrease in potential from 600 to 300 volt. The recording material can be charged to a maximum of more than 1,500 volt, which is substantially above the surface potential required in copying machines (about 700 volt), and is hence very useful for the copying sector.

USE EXAMPLES 6 TO 10

55 parts of a copolymer containing 70% of styrene, 6% of maleic anhydride and 24% of acrylic acid and having a mean molecular weight of about 2,000, 45 parts of one of the triazolopyrimidines shown in Table 2, and 0.3 part of methyl violet (C.I. 42535) are dissolved in ethyl acetate, the solution is applied onto an electrolytically roughened and subsequently anodized aluminum sheet of 0.15 mm thickness, which constitutes the electrically conductive base, the solvent is evaporated off in the air and drying is carried out for 30 minutes at 85° C., the resulting layer being 4 μm thick. The xerographic measurements are summarized in Table 2.

COMPARATIVE EXAMPLES 1 TO 3

The recording material is produced as described in Use Examples 6 to 10, except that, instead of the triazolopyrimidines stated in those Examples, the following pyrimidine derivatives are used as charge carrier-transporting compounds:

| Comparative Example | Triazolo[4,5-d]pyrimidine |
|---|---|
| 1 | 2-(4'-methoxyphenyl)-5-dimethylamino-7-dodecathio- |
| 2 | 2-(4'-methoxyphenyl)-5-dimethylamino-7-morpholino- |
| 3 | 2-(4'-methoxyphenyl)-5-dimethylamino-7-cyclohexylamino- |

The xerographic measurements on these recording materials are summarized in Table 2.

TABLE 2

| | Triazolo-pyrimidine from Example | Measured values | | | | | |
|---|---|---|---|---|---|---|---|
| Use | | A [ms] | C [V] | D [%] | E [%] | F [V/s] | G [V] |
| Example | | | | | | | |
| 6 | 7.3 | 190 | 1,700 | 19 | 93 | −6,050 | 1,260 |
| 7 | 8.3 | 200 | 1,550 | 24 | 89 | −5,300 | 1,070 |
| 8 | 1.3 | 150 | 1,600 | 27 | 96 | −6,950 | 1,100 |
| 9 | 4 | 160 | 1,100 | 40 | 97 | −5,500 | 640 |
| 10 | 3 | 165 | 1,250 | 31 | 94 | −5,900 | 820 |
| Comparative Example | | | | | | | |
| 1 | | — | 1,560 | 38 | 3 | −220 | — |
| 2 | | — | 450 | 36 | 4 | −340 | — |
| 3 | | — | 1,280 | 49 | 5 | −200 | — |

USE EXAMPLE 11

50 parts of a copolymer containing 60% of styrene and 40% of monomethyl maleate and having a mean molecular weight $\overline{M}_w$ of 10,000, 50 parts of 2-(4'-diethylaminophenyl)-5-diethylamino-7-chlorotriazolo[4,5-d]pyrimidine (Example 1.3) and 0.2 part of crystal violet (C.I. 42555) are applied, from a 5% strength solution in tetrahydrofuran, onto an electrolytically roughened and anodized aluminum foil of 0.15 mm thickness to give a layer which is about 4 μm thick when dry.

This printing plate is charged by means of a high-voltage corona and then exposed imagewise in a camera for 25 seconds. The plate is then developed with a powder toner, which is baked at 160° C. to give an abrasion-resistant surface. The non-toned area of the layer is washed off with a mixture of 0.5% of sodium carbonate, 25% of isopropanol and 74.5% of water, the aluminum surface being bared by this exposure. The solutions are applied onto the layer by brushing with a cottonwool ball. The differentiation between hydrophilic and oleophilic area, which is desirable in offset printing, is obtained, the surface of the base constituting the hydrophilic areas.

After treatment with the alkaline liquid, the printing plate is washed with water, and the hydrophilic character of the base surface is further increased by wiping it over with dilute phosphoric acid solution. The plate is inked with a fatty ink and then used for printing in a conventional manner on an offset printing machine.

USE EXAMPLE 12

50 parts of a copolymer containing 60% of styrene, 35% of methacrylic acid and 5% of maleic anhydride (K value 39.5, softening point about 225° C.), 50 parts of 2-(4'-diethylaminophenyl)-5-diethylamino-7-n-butoxytriazolo[4,5-d]pyrimidine (Example 37) and 0.2 part of C.I. Basic Violet 10, C.I 45174 base (rhodamine B base), are applied, from a 5% strength solution in tetrahydrofuran, onto an electrolytically roughened and anodized aluminum foil of 0.15 mm thickness to give a layer which is about 4 μm thick when dry.

The printing plate obtained is then treated further as described in Use Example 11, paragraphs 2 and 3. The resulting printing plate can be used in a conventional manner on offset printing machines.

Similar printing plates are obtained if, instead of the triazolopyrimidine compound stated in paragraph 1, one of the following compounds is used:

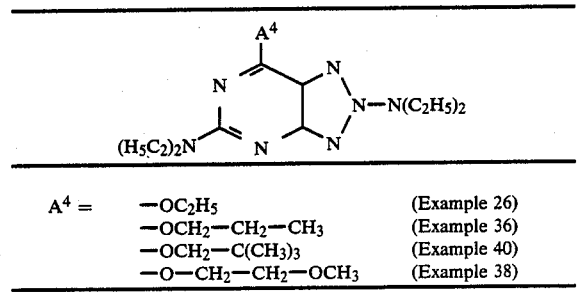

| $A^4 =$ | —OC$_2$H$_5$ | (Example 26) |
|---|---|---|
| | —OCH$_2$—CH$_2$—CH$_3$ | (Example 36) |
| | —OCH$_2$—C(CH$_3$)$_3$ | (Example 40) |
| | —O—CH$_2$—CH$_2$—OCH$_3$ | (Example 38) |

We claim:

1. A 2-H-v-triazolo[4,5-d]pyrimidine of the formula

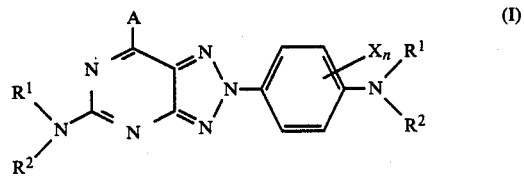

where $R^1$ and $R^2$ independently of one another are each $C_1$-$C_4$-alkyl, phenyl which is unsubstituted, or phenylalkyl of, in total, 7 to 10 carbon atoms, or

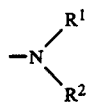

is a morpholino, piperidino, pyrrolidinyl or N'-$C_1$-$C_4$-alkylpiperazinyl group, and the two

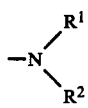

groups can be identical or different, X is $C_1$-$C_4$-alkyl, halogen or phenyl, n is 0, and A is (a)

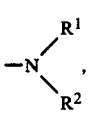

where $R^1$, $R^2$ and

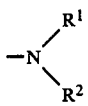

have the above meanings,
(b) hydrogen, halogen, cyano or thiocyano,
(c) $C_1$-$C_6$-alkoxy, $C_1$-$C_8$-alkoxy-$C_2$- or —$C_3$-alkoxy, phenoxy which is unsubstituted, phenylalkoxy of, in total, 7 to 10 carbon atoms, $C_1$-$C_{12}$-alkylthio, phenylthio which is unsubstituted, or —S—($CH_2$-$)_m$—$COOR^3$,
(d) $C_1$-$C_4$-alkylsulfonyl or
(e) $C_5$-$C_8$-cycloalkylamino,

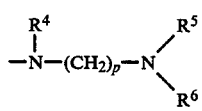

or —N—($CH_2$)$_2$—$NH_2$,
(f)

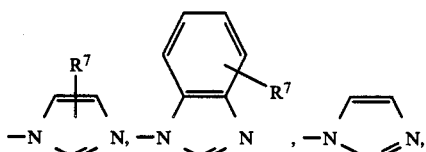

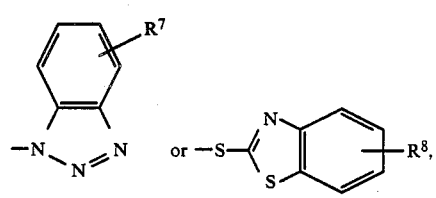

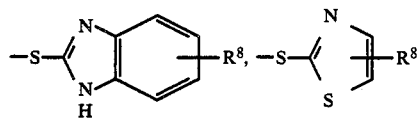

(g)
or

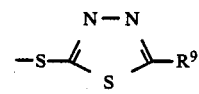

and where $R^3$ is $C_1$-$C_4$-alkyl, m is 1, 2, 3 or 4, $R^4$ is hydrogen or $C_1$-$C_4$-alkyl, $R^5$ and $R^6$ independently of one another are each $C_1$-$C_4$-alkyl, or

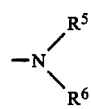

is a morpholino, piperidino, pyrrolidinyl or N'-$C_1$-$C_4$-alkylpiperazinyl group, p is 2, 3, 4 or 5, $R^7$ and $R^8$ independently of one another are each hydrogen, $C_1$-$C_4$-alkyl, nitro, halogen or phenyl, and $R^9$ is $C_1$-$C_4$-alkyl, phenyl, or $C_1$-$C_4$-alkylthio.

2. A triazolopyrimidine as defined in claim 1, wherein $R^1$ and $R^2$ are each methyl, ethyl, phenyl or benzyl, or

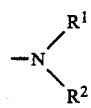

is pyrrolidinyl, piperidino, morpholino or 4-$C_1$-$C_4$-alkylpiperazinyl, n is 0 and A is
(a.1) dimethylamino, diethylamino, N-morpholino, N-piperidino, N-pyrrolidinyl or N'-$C_1$-$C_4$-alkylpiperazinyl,
(b.1) hydrogen or cholorine,
(c.1) $C_1$-$C_6$-alkoxy, 2-methoxyethoxy, 2-ethoxyethoxy, phenoxy, benzyloxy, thiobutyl or thiophenyl,
(d.1) benzenesulfonyl,
(e.1)

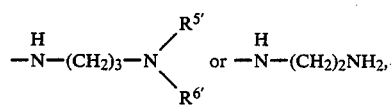

or
(f)

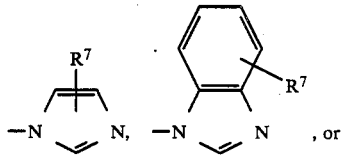

-continued

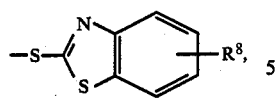

where $R^{5'}$ and $R^{6'}$ are each methyl or ethyl and $R^7$ and $R^8$ are each hydrogen or $-NO_2$.

3. A triazolopyrimidine of the formula

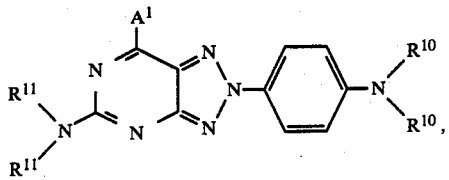

where $A^1$ is chlorine, bromine, $-S-(CH_2)_2-COOC_1-C_4$-alkyl, diethylamino, N-morpholino, N-piperidino, N-cyclohexylamino, $N'-C_1-C_4$-alkylpiperazinyl, imidazol-1-yl or $C_1-C_6$-alkoxy, and $R^{10}$ and $R^{11}$ independently of one another are each $C_1-C_4$-alkyl or phenyl.

4. A triazolopyrimidine as defined in claim 3, wherein $A^1$ is chlorine, $-S-(CH_2)_2-COOCH_3$, diethylamino, N-morpholino, N-piperidino, N-cyclohexylamino, 4-methylpiperazinyl, imidazol-1-yl, methoxy, ethoxy, n-propoxy, n-butoxy or 2,2-dimethylpropoxy, and $R^{10}$ and $R^{11}$ are identical or different and are each methyl, ethyl or phenyl.

5. A triazolopyrimidine as defined in claim 3, wherein the radicals

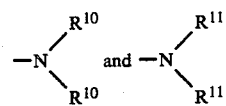

are identical or different and are each dimethylamino, diethylamino or diphenylamino.

6. A triazolopyrimidine as defined in claim 3, wherein $A^1$ is chlorine, $-S-(CH_2)_2-COOCH_3$, diethylamino, methoxy, ethoxy, n-propoxy, n-butoxy or 2,2-dimethylpropoxy.

7. A triazolopyrimidine as defined in claim 5, wherein $A^1$ is chlorine, $-S-(CH_2)_2-COOCH_3$, diethylamino, methoxy, ethoxy, n-propoxy, n-butoxy or 2,2-dimethylpropoxy.

8. A triazolopyrimidine of the formula

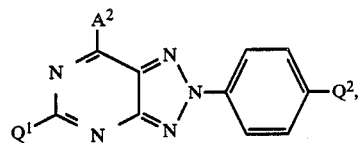

where $A^2$ is chlorine, $-S-(CH_2)_2-COCH_3$, diethylamino, methoxy, ethoxy, n-propoxy, n-butoxy or 2,2-dimethylpropoxy, $Q^1$ is dimethylamino or diethylamino, and $Q^2$ is diphenylamino, dimethylamino or diethylamino.

9. A triazolopyrimidine as defined in claim 8, wherein $A^2$ is chlorine, methoxy or diethylamino, and $Q^1$ and $Q^2$ are each diethylamino.

10. A triazolopyrimidine as defined in claim 8, wherein $A^2$ is chlorine or methoxy, and $Q^1$ and $Q^2$ are each diethylamino.

* * * * *